United States Patent
Ahmad

(10) Patent No.: US 10,357,476 B1
(45) Date of Patent: Jul. 23, 2019

(54) METHOD FOR TREATING CORONARY ARTERY DISEASE

(71) Applicant: Anis Ahmad, Rock Island, IL (US)

(72) Inventor: Anis Ahmad, Rock Island, IL (US)

( * ) Notice: Subject to any disclaimer, the term of this patent is extended or adjusted under 35 U.S.C. 154(b) by 0 days.

(21) Appl. No.: 16/186,495

(22) Filed: Nov. 10, 2018

Related U.S. Application Data

(60) Provisional application No. 62/753,052, filed on Oct. 30, 2018.

(51) Int. Cl.
| | | |
|---|---|---|
| *C07K 16/40* | (2006.01) | |
| *A61K 31/403* | (2006.01) | |
| *A61K 31/155* | (2006.01) | |
| *A61K 39/395* | (2006.01) | |
| *A61P 9/10* | (2006.01) | |
| *A61K 31/505* | (2006.01) | |
| *A61K 31/40* | (2006.01) | |
| *A61K 31/22* | (2006.01) | |
| *A61K 31/366* | (2006.01) | |

(52) U.S. Cl.
CPC .......... *A61K 31/403* (2013.01); *A61K 31/155* (2013.01); *A61K 31/22* (2013.01); *A61K 31/366* (2013.01); *A61K 31/40* (2013.01); *A61K 31/505* (2013.01); *A61K 39/3955* (2013.01); *A61P 9/10* (2018.01)

(58) Field of Classification Search
None
See application file for complete search history.

(56) References Cited

U.S. PATENT DOCUMENTS

| | | | |
|---|---|---|---|
| 4,503,067 | A | 3/1985 | Wiedemann et al. |
| 6,699,997 | B2 | 3/2004 | Hildesheim et al. |
| 7,056,942 | B2 | 6/2006 | Hildesheim et al. |
| 7,126,008 | B2 | 10/2006 | Hildesheim et al. |
| 7,268,156 | B2 | 9/2007 | Brook et al. |
| 8,492,426 | B1 | 7/2013 | Ahmad |
| 2003/0073729 | A1 | 4/2003 | Kitihara et al. |
| 2005/0009897 | A1 | 1/2005 | Anderson et al. |
| 2006/0154959 | A1 | 7/2006 | Cornett et al. |
| 2007/0208073 | A1 | 9/2007 | Bryson |
| 2018/0195122 | A1* | 7/2018 | Kornman ............ C12Q 1/6883 |

FOREIGN PATENT DOCUMENTS

| | | |
|---|---|---|
| CN | 101417132 | 12/2010 |
| WO | 2011161161 | 12/2011 |

OTHER PUBLICATIONS

Attwood (Science 2000 290:471-473).*
Skolnick et al. (Trends in Biotech. 2000, 18:34-39).*
Ahmad, A. "A Cure for Coronary Artery Disease," J. Diabetes Metab. 2017, 8, 769.
Ahmad, A. "Carvedilol Can Replace Insulin in the Treatment of Type 2 Diabetes," J. Diabetes Metab. 2017, 8, 726.
Ayashi, S., et al. "Role of Antioxidant Property of Carvedilol in Mild to Moderate Hypertensive Patients: A Prospective Open-Label Study," Indian J. Pharmacol. 2016, 48(4), 372-76.
Bakris, G. L., et al. "Metabolic Effects of Carvedilol vs. Metoprolol in Patients with Type 2 Diabetes Mellitus and Hypertension: A Randomized Controlled Trial," J. Am. Med. Assoc. 2004, 292(18), 2227-36.
Bell, D. S. H., et al. "Comparison of Carvedilol and Metoprolol on Serum Lipid Concentration in Diabetic Hypertensive Patients," Diab. Obes. Met. 2009, 11, 234-38.
Blake, G. J., et al. "Are Statins Anti-Inflammatory?" Curr. Control. Trials Cardiovasc. Med. 2000, 1, 161-65.
Centers for Disease Control and Prevention, "Heart Disease Facts," available at www.cdc.gov/heartdisease/facts.htm.
Chawla, A., et al. "Microvascular and Macrovascular Complications in Diabetes Mellitus: Distinct or Continuum?" Indian J. Endocrinol. Metab. 2016, 20, 546-51.
Dave, T., et al. "Plaque Regression and Plaque Stabilisation in Cardiovascular Diseases," Indian J. Endocrinol. Metab. 2013, 17, 983-89.
Feng, X., et al. "Low ApoA-1 is Associated with Insulin Resistance in Patients with Impaired Glucose Tolerance: A Cross-Sectional Study," Lipids Health Dis. 2017, 16, 69.
Ferner, R. E. "Drug-Induced Diabetes," Baillière's Clin. Endocrinol. Metab. 1992, 6, 849-66.
Janus, A, et al. "Insulin Resistance and Endothelial Dysfunction Constitute a Common Therapeutic Target in Cardiometabolic Disorders," Mediators Inflamm. 2016, 3634948.
Jousilahti, P., et al. "Sex, Age, Cardiovascular Risk Factors, and Coronary Heart Disease: A Prospective Follow-Up Study of 14786 Middle-Aged Men and Women in Finland," Circulation, 1999, 99, 1165-72.
Kovanen, P.T., et al. "Pharmacologic Prevention of Coronary Plaque Rupture—The Major Cause of Acute Coronary Syndromes," Heart Metab. 2007, 36, 9-14.
Kveiborg, B., et al. "Metoprolol Compared to Carvedilol Deteriorates Insulin-Stimulated Endothelial Function in Patients with Type 2 Diabetes—A Randomized Study," Cardiovasc. Diabetol. 2010, 9(21), 1-11.
Levy, A.P., et al. "Intraplaque Hemorrhage," Curr. Mol. Med. 2006, 6(5), doi: 10.2174/156652406778018626.

(Continued)

*Primary Examiner* — Sharon X Wen
(74) *Attorney, Agent, or Firm* — Hojka Qadeer, LLC; Umair A. Qadeer

(57) ABSTRACT

The use of a combination of carvedilol, metformin, evolocumab, and one or more statins to remove atheromas from coronary arteries and thereby treat coronary artery disease is disclosed. The method treats coronary artery disease by removing one or more atheromas from one or more coronary arteries of a patient by administering a therapeutically effective amount of: (a) carvedilol; (b) metformin; (c) evolocumab; and (d) one or more statins; or a pharmaceutically acceptable salt, prodrug, or derivative of one or more of (a)-(d). In some embodiments, the one or more statins comprise simvastatin. In some embodiments, the one or more statins comprise rosuvastatin. In some embodiments, the one or more statins comprise atorvastatin. In some embodiments, the one or more statins comprise pravastatin.

5 Claims, No Drawings

(56) References Cited

OTHER PUBLICATIONS

Libby, P., et al. "Inflammation and Atherosclerosis," Circulation, 2002, 105, 1135-43.
Miccoli, R., et al. "Insulin Resistance and Lipid Disorders," Future Lipidology, 2008, 3(6), 651-664.
Minuz, P., et al. "Antiplatelet Activity of β-blockers: New Light on Existing Data," Br. J. Clin. Pharmacol. 2014, 78, 937-39.
Moreno, P.R. "Vulnerable Plaque: Definition, Diagnosis and Treatment," Cardiol. Clin. 2010, 28, 1-30.
Mozaffarian, D. "Heart Disease and Stroke Statistics—2015 Update," Circulation, 2015, e29.
Musunuru, K. "Atherogenic Dyslipidemia: Cardiovascular Risk Factors and Dietary Intervention," Lipids, 2010, 45, 907-14.
Nicholls, S. J., et al. "Effect of Evolocumab on Progression of Coronary Disease in Statin-Treated Patients: The GLAGOV Randomized Clinical Trial," J. Am. Med. Assoc. 2016, 316(22), 2373-84.
Nissen, S. E., et al. "Effect of Recombinant ApoA-I Milano on Coronary Atherosclerosis in Patients with Acute Coronary Syndrome: A Randomized Controlled Trial," J. Am. Med. Assoc. 2003, 290, 2292-300.
Saisho, Y. "Metformin and Inflammation: Its Potential Beyond Glucose-Lowering Effect," Endocr. Metab. Immune Disord. Drug Targets, 2015, 15, 196-205.
Spagnoli, L. G., et al. "Role of Inflammation in Atherosclerosis," J. Nucl. Med. 2007, 48, 1800-15.
Takata, K., et al. "Stabilisation of High-Risk Plaques," Cardiovasc. Diagn. Ther. 2016, 6, 304-21.
Yuan, Z., et al. "Cardioprotective Effects of Carvedilol on Acute Autoimmune Myocarditis: Anti-Inflammatory Effects Associated with Antioxidant Property," Am. J. Physiol. Heart Circ. Physiol. 2004, 286, H83-H90.

\* cited by examiner

METHOD FOR TREATING CORONARY ARTERY DISEASE

CROSS-REFERENCE TO RELATED APPLICATIONS

This application claims priority to U.S. Provisional Patent Application Ser. No. 62/753,052, filed on Oct. 30, 2018, the disclosure of which is incorporated herein in its entirety by reference.

BACKGROUND

Field of the Invention

The present disclosure relates to the use of a combination of carvedilol, metformin, evolocumab, and one or more statins to treat coronary artery disease.

Description of the Related Art

Coronary artery disease, a condition affecting the arteries that supply the heart with blood, is usually caused by atherosclerosis. Atherosclerosis is the buildup of plaque inside artery walls. This buildup narrows the inside of arteries and thereby restricts the flow of blood therein. This abnormal accumulation of material inside an artery wall is known as an atheroma or atheromatous plaque.

Individuals with coronary artery disease generally have multiple atheromas in their coronary arteries. Atheromas may rupture or become ulcerated, leading to the formation of a thrombus on the ulcerated area of the atheroma or on the ruptured atheromatous plaque. See, e.g., Moreno, P. R. "Vulnerable Plaque: Definition, Diagnosis and Treatment," *Cardiol. Clin.* 2010, 28, 1-30. This may lead to obstruction of the coronary artery, causing unstable angina, acute myocardial infarction, or death. See, e.g., Kovanen, P. T., et al. "Pharmacologic Prevention of Coronary Plaque Rupture—The Major Cause of Acute Coronary Syndromes," *Heart Metab.* 2007, 36, 9-14. According to the Centers for Disease Control 610,000 people die from heart disease every year in the United States, including over 370,000 who die from coronary heart disease. See Centers for Disease Control and Prevention, "Heart Disease Facts," available at www.cdc.gov/heartdisease/facts.htm The risk factors for coronary artery disease include hypertension, diabetes mellitus, smoking, hyperlipidemia, obesity, metabolic syndrome, sleep apnea, a diet rich in saturated fats and trans fats, lack of physical activity, age, gender, and genetic history. Age, gender, and genetic history are obviously untreatable risk factors, but the remaining risk factors may be treated in various ways.

Atheroma formation is triggered by a number of factors, including the aforementioned risk factors for coronary artery disease. A significant risk factor for atheroma formation is the development of insulin resistance, which promotes endothelial dysfunction. See, e.g., Janus, A., et al. "Insulin Resistance and Endothelial Dysfunction Constitute a Common Therapeutic Target in Cardiometabolic Disorders," *Mediators Inflamm.* 2016, 2016, 3634948; Bell, D. S., et al. "Comparison of Carvedilol and Metoprolol in Serum Lipid Concentration in Diabetic Hypertensive Patients," *Diab. Obes. Met.* 2009, 11, 234-38; Miccoli, R., et al. "Insulin Resistance and Lipid Disorders," *Future Lipidology,* 2008, 3, 651-54. Various drugs may increase insulin resistance, including thiazide diuretics, various β-blockers, steroids, and antipsychotic drugs, thereby increasing the risk of atheroma formation. See, e.g., Ferner, R. E. "Drug Induced Diabetes," Baillière's *Clin. Endocrinol. Metab.* 1992, 6, 849-66; Ahmad, A. "Carvedilol Can Replace Insulin in the Treatment of Type 2 Diabetes," *J. Diabetes Metab.* 2017, 8, 726. Inflammation of the coronary arteries is another significant risk factor. See, e.g., Libby, P., et al. "Inflammation in Arteriosclerosis," *Circulation,* 2002, 105, 1135-43; Spagnoli, L. G., et al. "Role of Inflammation in Atherosclerosis," *J. Nucl. Med.* 2007, 48, 1800-15. The combination of coronary artery inflammation and insulin resistance may synergistically increase the severity of coronary artery disease. Atherogenic dyslipidemia and other lipid disorders also increase the risk of atheroma formation. See, e.g., Musunuru, K. "Atherogenic Dyslipidemia: Cardiovascular Risk Factors and Dietary Intervention," *Lipids,* 2010, 45, 907-14.

Atheroma development begins with the formation of fatty streaks on the endothelium, a thin monocellular layer that covers the entire inner surface of blood vessels and separates circulating blood from tissues. Atheroma formation progresses via accumulation of material in the tunica intima between the endothelial lining and the smooth muscle layer of the arterial wall. The accumulated material mainly consists of macrophage cells, debris, lipids, calcium, and a variable amount of fibrous connective tissue. The accumulated material forms a swelling in the arterial wall, which may intrude into the lumen of the artery, thereby narrowing the artery and restricting blood flow. This lesion is referred to as an atheromatous plaque.

Atheromatous plaques may be stable or unstable. An unstable atheromatous plaque has a thin fibrous cap that is prone to rupture. Unstable plaques contain a large lipid pool consisting of oxidized low-density lipoprotein (LDL), apoB, and cholesterol. This liquid pool may increase in size. Unstable plaques also have heavy inflammatory cell infiltration, including monocytes, macrophages, and T cell lymphocytes. Moreover, debris from ruptured macrophages that were previously overloaded with lipids attracts more macrophages.

An atheromatous plaque may grow and protrude into the coronary artery lumen. An atheromatous plaque may exhibit overgrowth of the vasa vasorum, a network of small blood vessels that supply the walls of large blood vessels. The plaque may rupture, leading to the formation of a large thrombus that may severely or completely obstruct the coronary artery. Hemorrhage may also occur in the plaque.

High-risk atherosclerotic plaques may be evaluated using imaging technologies including optical coherence tomography (OCT), intravascular ultrasound-derived virtual histology, and infrared spectroscopy.

While various treatments for the underlying causes of atheroma formation are known, no single treatment or combination therapy that treats all the major causative factors of atheroma formation is known. The complete removal of atheromas from coronary arteries would cure coronary artery disease. Thus, there remains an unmet clinical need for a treatment regimen that treats all major causative factors of atheroma formation and thereby cures coronary artery disease.

SUMMARY

The use of a combination of carvedilol, metformin, evolocumab, and one or more statins to remove atheromas from coronary arteries and thereby treat coronary artery disease is disclosed herein.

A method of treating coronary artery disease by removing one or more atheromas from one or more coronary arteries of a patient comprising administering a therapeutically effective amount of: (a) carvedilol; (b) metformin; (c) evolocumab; and (d) one or more statins; or a pharmaceutically acceptable salt, prodrug, or derivative of one or more of (a)-(d) is described herein. In some embodiments, the one or more statins comprise simvastatin. In some embodiments, the one or more statins comprise rosuvastatin. In some embodiments, the one or more statins comprise atorvastatin. In some embodiments, the one or more statins comprise pravastatin.

DETAILED DESCRIPTION OF THE ILLUSTRATED EMBODIMENTS

The use of a combination of carvedilol, metformin, evolocumab, and one or more statins to remove atheromas from coronary arteries and thereby treat coronary artery disease is disclosed herein.

A method of treating coronary artery disease by removing one or more atheromas from one or more coronary arteries of a patient comprising administering a therapeutically effective amount of: (a) carvedilol; (b) metformin; (c) evolocumab; and (d) one or more statins; or a pharmaceutically acceptable salt, prodrug, or derivative of one or more of (a)-(d) is described herein. In some embodiments, the one or more statins comprise simvastatin. In some embodiments, the one or more statins comprise rosuvastatin. In some embodiments, the one or more statins comprise atorvastatin. In some embodiments, the one or more statins comprise pravastatin.

Agents Used in Treatment Regimen

Carvedilol (±)-1-(carbazol-4-yloxy-3-[[2-(o-methoxyphenoxy)ethyl]amino]-2-propanol, also known as carvedilol, is a third-generation β-blocker that blocks β1, β2, and a adrenergic receptors. Carvedilol is claimed in U.S. Pat. No. 4,503,067. Methods of preparing carvedilol and related crystalline solids of carvedilol, processes for the manufacture thereof, and pharmaceutical compositions thereof are claimed in U.S. Pat. Nos. 6,699,997, 6,710,184, 7,056,942, and 7,126,008.

Carvedilol is used in the treatment of hypertension, coronary artery disease, and congestive heart failure. Carvedilol reduces insulin resistance and stimulates insulin receptors. See, e.g., U.S. Pat. No. 8,492,426; Muniz, P., et al. "Antiplatelet Activity of β-blockers: New Light on Existing Data," *Br. J. Clin. Pharmacol.* 2014, 78, 937-39; Bakris, G. L., et al. "Metabolic Effect of Carvedilol vs. Metoprolol with Hypertension," *J. Am. Med. Assoc.* 2004, 18, 2227-36. Carvedilol also exhibits anti-inflammatory properties. See, e.g., Yuan, Z., et al. "Cardioprotective Effects of Carvedilol on Acute Autoimmune Myocarditis: Anti-Inflammatory Effects Associated with Antioxidant Property," *Am. J. Physiol. Heart Circ. Physiol.* 2004, 286, 83-90.

Carvedilol promotes normal endothelial function. Normal or antiatherogenic functions of the endothelium include vasodilation, thrombolysis, platelet disaggregation, antiproliferation, anti-inflammation, and antioxidation. Carvedilol promotes all of these functions except thrombolysis.

Endothelial dysfunction may be caused by insulin resistance and oxidized low-density lipoprotein (LDL). Endothelial dysfunction may lead to vasoconstriction, thrombosis, adhesion molecule dysregulation, inflammation, and oxidant activity.

Carvedilol also increases the level of HDL. ApoA-1, an important part of high density lipoprotein (HDL), also promotes normal endothelial function. ApoA-1 is an antioxidant and anti-inflammatory agent, and it scavenges toxic phospholipids, stimulates reverse cholesterol transport, exhibits antithrombotic and profibrinolytic effects, and attenuates endothelial dysfunction. See, e.g., Feng, X., et al. "Low ApoA-1 is Associated with Insulin Resistance in Patients with Impaired Glucose Tolerance Test: A Cross-Sectional Study," *Lipids Health Dis.* 2017, 16, 69.

A standard carvedilol dosage is 25 mg administered twice per day. Common side effects of using carvedilol include low blood pressure, bradycardia, dizziness, drowsiness, nausea, vomiting, diarrhea, dry eyes, fatigue, joint pain, cough, and decreased sex drive.

Metformin 1,1-dimethylbiguanide, also known as metformin, is a biguanide hypoglycemic agent used to treat diabetes mellitus. Metformin was first described in 1922. See Werner, E. A., et al. "The Preparation of Methylguanidine, and of ββ-Dimethylguanidine by the Interaction of Dicyandiamide, and Methylammonium and Dimethylammonium Chlorides Respectively," *J. Chem. Soc.*, Trans. 1922, 121, 1790-95. Metformin reduces insulin resistance, and also has anti-inflammatory properties. See Saisho, Y. "Metformin and Inflammation: Its Potential Beyond Glucose-Lowering Effect," *Endocr. Metab. Immune Disord. Drug Targets,* 2015, 15, 196-205. In addition, metformin prevents platelet aggregation. Metformin also lowers total cholesterol and LDL levels, but increases the level of HDL. Its side effects include nausea, vomiting, diarrhea, and lactic acidosis, and it cannot be used in patients with renal failure, liver failure, or serious infections.

Evolocumab

Evolocumab is a monoclonal antibody and a PCSK9 inhibitor. It is used to treat hyperlipidemia. Combination therapy using evolocumab at its maximum dose along with statins may significantly lower LDL levels. See, e.g., Nicholls, S. J., et al. "Effect of Evolocumab on Progression of Coronary Artery Disease in Statin-Treated Patients: The GLAGOV Randomized Clinical Trial," *J. Am. Med. Assoc.* 2016, 16, 2373-84.

The use of evolocumab has reduced the incidence of acute myocardial infarction (MI) and acute cerebrovascular accident (CVA) among patients with heterozygous or homozygous familial hypercholesterolemia.

Evolocumab is administered subcutaneously; therefore, there may be pain, swelling, and redness at the site of injection. Side effects of evolocumab include acute infection of the nose, throat, or sinuses. Standard evolocumab dosages are 140 mg administered twice per month or 240 mg administered once per month.

Statins

Statins are HMG-CoA (HMOA) reductase inhibitors used to lower cholesterol and LDL levels. Certain statins, namely simvastatin and rosuvastatin, also increase HDL levels. Statins are also anti-inflammatory agents. Blake, G. J., et al. "Are Statins Anti-Inflammatory?" *Curr. Control. Trials Cardiovasc. Med.* 2000, 1, 161-65. When used as a secondary prevention measure for acute myocardial infarction, statins lower the rate of relapse by 30%.

While statins also increase insulin resistance, they decrease cardiovascular morbidity and mortality. See, e.g., Ferner, R. E. "Drug Induced Diabetes," *Baillière's Clin.*

*Endocrinol. Metab.* 1992, 6, 849-66. Statins inhibit platelet function and vascular smooth muscle cell proliferation, and reduce the accumulation of inflammatory cells.

The use of statins may cause mild or severe muscle pain, jaundice, and abdominal pain. Rarely, statins can cause rhabdomyolysis with liver and kidney damage, especially if used at a high dose.

The average dose of atorvastatin is 40 mg daily, and the maximum dose is 80 mg daily. The average dose of simvastatin is 40 mg daily, and the maximum dose is 80 mg daily. The average dose of rosuvastatin is 10 mg daily, and the maximum dose is 40 mg daily.

Proposed Mechanisms of Action

The use of a combination of carvedilol, metformin, evolocumab, and one or more statins treats all the major causative factors of atheroma formation. This leads to complete removal of atheromas from coronary arteries and results in the curing of coronary artery disease.

Effect of Treatment Regimen on Insulin Resistance and Lipid Disorders

Insulin resistance decreases lipoprotein lipase activity, which increases apoB-lipoprotein, very-low-density lipoprotein (VLDL), LDL, and triglyceride levels. There is an increase in hepatic lipase activity that increases the removal of HDL and decreases HDL levels in the blood. While vasoconstricting β-blockers reduce HDL levels, carvedilol is a vasodilating β-blocker and increases HDL levels, while also decreasing LDL, VLDL, total cholesterol, and triglyceride levels. Carvedilol and metformin decrease insulin resistance and increase the activity of lipoprotein lipase, thereby decreasing the levels of apoB-lipoprotein, VLDL, LDL, and triglycerides. Carvedilol also prevents LDL oxidation. Evolocumab and statins lower LDL levels. Therefore, atherogenic dyslipidemia may be treated with carvedilol, metformin, evolocumab, and one or more statins.

Treatment of Stable Atheromatous Plaque in Coronary Artery

Stable atheromatous plaques may progress into unstable plaques due to insulin resistance. Nissen, S. E., et al. "Effect of Recombinant ApoA-1 Milano on Coronary Atherosclerosis in Patients of Acute Coronary Syndrome: A Randomized Controlled Trial," *J. Am. Med. Assoc.* 2003, 290, 2292-300. Carvedilol and metformin decrease insulin resistance, thereby improving plaque stability and preventing the progression of a stable plaque into an unstable plaque. See Takata, K., et al. "Stabilisation of High Risk Plaque," *Cardiovasc. Diagn. Ther.* 2016, 6, 304-21.

The levels of apoA-1 are low in patients with coronary artery disease due to increased insulin resistance; carvedilol and metformin decrease insulin resistance and increase the level of apoA-1. Moreover, apoA-1 is the major component of HDL, and HDL levels are also increased by carvedilol and metformin. Simvastatin and rosuvastatin also increase HDL levels. Thus, HDL and apoA-1 levels may be increased by several methods.

The supply of LDL and apoB to the lipid pool of the atheroma is markedly reduced by treatment with evolocumab and one or more statins. Additionally, LDL oxidation is prevented by carvedilol. LDL, apoB, and other toxic lipids from the lipid pool are removed by HDL and apoA-1. ApoA-1 also removes toxic phospholipids.

Statins treat inflammation in the atheroma, but are only partially effective. The combination of statins with carvedilol, metformin, and apoA-1 may reduce inflammation in the plaque. Smooth muscle cells proliferate under conditions of insulin resistance, and their proliferation may be reversed by decreasing insulin resistance with carvedilol and metformin.

Carvedilol also has anti-proliferation properties, which may reverse smooth muscle cell proliferation. The proteases produced by macrophages remove smooth muscle cells and degrade collagen fibers. The extracellular matrix is damaged by MMP-9, which is an enzyme produced by macrophages. See Feng, X., et al. "Low ApoA-1 is Associated with Insulin Resistance in Patients with Impaired Glucose Tolerance Test: A Cross-Sectional Study," *Lipids Health Dis.* 2017, 16, 69. As a result, the atheroma may rupture or ulcerate, and a thrombus may form on the ulcerated area. The treatment of these two conditions and intra-plaque hemorrhage is similar to the treatment of unstable plaques. With combination drug therapy including carvedilol, metformin, evolocumab, and one or more statins, the material contained within the atheroma may be removed. Following the reduction of the lipid pool, inflammatory cells, and smooth muscle wall hypertrophy, healthy macrophages will infiltrate and remove the debris. The atheroma will then be reduced to a fibrous nodule on the intima, which may be removed by endothelial fibrinolysis. See Bell, D. S., et al. "Comparison of Carvedilol and Metoprolol in Serum Lipid Concentration in Diabetic Hypertensive Patients," *Diab. Obes. Met.* 2009, 11, 234-38. Thereafter, the process of coronary artery repair may begin.

Treatment of Unstable Atheromatous Plaque in Coronary Artery

To achieve the goal of entirely removing atheromas from the coronary artery, the risk factors for coronary artery disease must first be controlled. Unstable atheromatous plaques form on account of insulin resistance, which is treated with carvedilol and metformin, increasing plaque stability. Treatment of insulin resistance may also repress MMP-9 secretion. MMP-9 secretion causes the thinning of the fibrous cap, and therefore inhibition of MMP-9 secretion leads to fibrous cap thickening and reduces the risk of rupture. Statins also inhibit MMP-9 secretion by macrophages and damaged endothelial cells. MMP-9 dissolves the extracellular matrix and increases the risk of plaque rupture, and amelioration of insulin resistance represses MMP-9. See Feng, X., et al. "Low ApoA-1 is Associated with Insulin Resistance in Patients with Impaired Glucose Tolerance Test: A Cross-Sectional Study," *Lipids Health Dis.* 2017, 16, 69. The large lipid-rich necrotic core of the plaque, which contains oxidized LDL and apoB, may be treated by decreasing the supply of LDL and apoB with statin therapy combined with evolocumab.

Carvedilol also prevents LDL oxidation. The removal of LDL and other toxic lipids from the lipid-rich necrotic area may be achieved by apoA-1 and HDL, whose levels in the blood are increased by the combination drug therapy as explained above.

Therefore, eliminating the lipid supply and removal of the lipids from the atheroma will severely shrink the lipid core of the atheroma. Macrophages sometimes become overloaded with oxidized lipoprotein particles and become foam cells. Some of these cells die, releasing fat- and cholesterol-laden membranes in the intercellular space, which attracts more macrophages. The macrophage-induced enzymes erode the fibrous membrane beneath the endothelium so that the cover separating the plaque from the blood flow in the lumen becomes thin and fragile. When this occurs, the proper treatment is to reduce the supply of LDL and apoB, prevent LDL oxidation, and remove LDL, apoB, cholesterol, and toxic lipids via the actions of HDL and apoA-1. The macrophages will shrink and be eliminated by anti-inflammatory agents and hyperinsulinemia, as hyperinsulinemia due to insulin resistance accelerates macrophage death.

Anti-inflammatory drugs, such as statins, carvedilol, metformin, and apoA-1, eliminate inflammation. Changes in apoA-1 are negatively correlated with high-sensitivity C-reactive protein levels, as apoA-1 has anti-inflammatory and antithrombotic effects. Smooth muscle cell proliferation is not present in unstable plaques as smooth muscle cells are removed by macrophages. The plaque may rupture, and an atheroma may form on the ruptured plaque. However, the formation of a thrombus on the plaque may be prevented by carvedilol, metformin, and apoA-1, as these agents prevent platelet aggregation.

Even if a thrombus forms, it will not be large and will not cause a major blockage of a coronary artery that can lead to unstable angina or acute myocardial infarction (MI). Instead, the thrombus will be small and will be dissolved by endothelial thrombolysis as endothelial function is improved by the drug therapy. Carvedilol and apoA-1 supplement the actions of vascular endothelium, and carvedilol reduces insulin resistance, thus preserving endothelial function.

Hemorrhage may occur inside the plaque, and this can be prevented by reversing the growth of the vasa vasorum. See, e.g., Chawla, A., et al. "Microvascular and Macrovascular Complications in Diabetes Mellitus," *Indian J. Endocrinol. Metab.* 2016, 20, 546-51. The vasa vasorum grows due to insulin resistance, which is reduced by carvedilol and metformin. Therefore, the proposed combination drug treatment may decrease the number of plaques. If hemorrhage occurs, the resultant thrombus will be small, as carvedilol, metformin, and apoA-1 prevent platelet aggregation. The thrombus will then be removed by endothelial thrombolysis. A thrombus may also form in the plaque from intraplaque hemorrhage; if present, the size of this type of thrombus will be small, as the vasa vasorum are atrophic. In both cases, thrombi are removed by endothelial thrombolysis. Subsequently, healthy macrophages infiltrate and remove debris, after which the plaque becomes a fibrous nodule that may be removed by endothelial fibrinolysis. The plaque is then completely removed.

Following treatment as described herein, the unstable plaque may develop a stable fibrous cap and the lipid core and inflammatory cells may be eliminated. Neovascularization may be markedly decreased or eliminated due to the reduction of insulin resistance by carvedilol and metformin treatment. If there is a thrombus in the plaque, it will be dissolved by endothelial thrombolysis. Healthy macrophages will then infiltrate and remove all debris and other waste. The plaque will then shrink to a small fibrous nodule on the intima of the coronary artery, which will be removed by endothelial fibrinolysis, thereby resulting in the complete removal of atheroma from the coronary artery.

Alternatively, if a plaque ruptures and causes major or total occlusion of a coronary artery, resulting in unstable angina or acute myocardial infarction, an appropriate treatment will be with percutaneous coronary intervention (PCI) or coronary artery bypass grafting.

Example

Coronary artery bypass grafting (CABG) and percutaneous transluminal coronary angioplasty (PTCA) are standard treatments for acute coronary syndrome and advanced coronary disease for about 70-80% of patients. Patients who cannot undergo CABG because of age or comorbidities and patients who cannot have PTCA because of previous adverse outcomes may be treated using the treatment regimen described above.

A patient who had undergone CABG and PTCA and had refractory angina was advised not to receive PTCA or CABG by her cardiologist after her most recent angiogram. The patient suffered from chest pain almost daily, which was relieved with nitroglycerin. The patient also had pain in both upper arms and both forearms lasting for several hours daily, and this pain did not respond to nitroglycerin. The patient also suffered from dyspnea, wheezing, and pedal edema.

An EKG showed no significant abnormality. A chest X-ray showed changes suggestive of congestive heart failure. The echocardiogram showed diastolic dysfunction and an ejection fraction of 60%.

A coronary angiogram was performed in 2013 and showed the following:
1. The main coronary artery showed no disease.
2. The left circumflex coronary artery gave rise to a moderately sized obtuse marginal coronary artery. The large obtuse marginal coronary was completely occluded. The proximal circumflex had a 70% lesion. The middle and distal circumflex had 70-80% long diffuse lesions.
3. The left anterior descending artery (LAD) gave rise to moderately sized diagonal left and right coronary arteries with diffuse disease. The proximal and middle LAD had 70-80% diffuse disease, and the distal LAD had 70% diffuse disease.
4. The right coronary artery was completely occluded in the proximal part.
5. The obtuse marginal coronary artery, which was occluded, was receiving its blood supply from a vein graft.
6. The left internal mammary artery graft had disease in the proximal part, and this graft did not provide much circulatory support for the LAD.
7. The vein graft to the right coronary artery had 50% diffuse disease.

Blood work performed in September 2017 showed an A1c level of 6.2, a total cholesterol level of 298 mg/dl, a triglyceride level of 421 mg/dl, and an HDL level of 47 mg/dl. The LDL level could not be determined because of high triglyceride levels. The blood work was repeated in January 2018 and showed a total cholesterol level of 194 mg/dl, a triglyceride level of 291 mg/dl, an HDL level of 53 mg/dl, and an LDL level of 83 mg/dl. The various ratios were excluded. The BNP level was 606.

The patient had smoked two and one-half packs of cigarettes per day for fifty (50) years and was trying hard to reduce smoking. She was now smoking one-half pack of cigarettes per day. The patient suffered from hypertension, chronic congestive heart failure, COPD, type 2 diabetes mellitus, peripheral neuritis, and osteoarthritis. The patient had an acute myocardial infarction in 2014.

The patient underwent CABG with three grafts in 2009 and PTCA with five stents in 2011. Additionally, the patient had a hysterectomy and cholecystectomy.

The patient received the following medications for the conditions described above:
1. carvedilol—25 mg twice per day;
2. metformin—500 mg twice per day;
3. pravastatin—80 mg daily;
4. bumetanide—1 mg daily;
5. aspirin—81 mg daily;
6. nitroglycerin patch—0.4 mg/hr daily;
7. glimepiride—4 mg twice per day;

8. nitroglycerin tablet—0.4 mg sublingual as needed;
9. evolocumab—140 mg every two weeks subcutaneously; and
10. albuterol—unit dose with a hand nebulizer for use every four (4) hours as needed.

The medications that were administered to remove the atheromas and thereby open the coronary arteries were carvedilol, metformin, pravastatin, and evolocumab.

The patient was free from chest pain, arm pain, dyspnea, and wheezing three (3) months after starting the treatment with carvedilol, metformin, pravastatin, and evolocumab. The other medications were continued. The pedal edema resolved much earlier. The coronary angiogram was repeated after eight months of treatment. The angiogram showed that the LAD and circumflex arteries and their branches were patent, and the right coronary artery was also patent. The grafts could not be observed. This finding indicated that all atheromatous plaques were eliminated and that the coronary artery disease was cured. Intravascular ultrasound was not used.

Advantages of Using Disclosed Treatment Regimen

The disclosed treatment regimen offers significant advantages over current treatments for patients with coronary artery disease.

For example, there is no standard treatment available for patients with coronary artery disease who have had CABG and PTCA and experience refractory angina. In addition, treatment using PTCA or CABG cannot be provided in 20-30% of patients because of advanced coronary artery disease. For such patients, no treatment is available to prevent the complications of advanced coronary artery disease, such as refractory angina, multiple episodes of acute myocardial infarction, and repeated episodes of acute pulmonary edema, arrhythmias, A-V block, peripheral vascular failure, cardiac arrest, and death. Such patients may be treated with the disclosed treatment regimen, and these complications may thus be prevented. Also, patients who cannot afford to have CABG or PTCA, such as many patients in developing countries, may be treated with the disclosed treatment regimen. Certain patients who refuse to receive PTCA or CABG may also be treated in the same way.

Patients who have intractable angina after PTCA and CABG continue to receive one or more stents placed in their coronary arteries because of multiple stenotic lesions. This stent placement may occur every year or even more often, with no relief of symptoms because no alternative treatment is available. The disclosed treatment regimen may relieve intractable angina for such patients and avoid the need to place multiple stents. Enhanced external counterpulsation therapy and other treatments for refractory angina will not be needed.

The disclosed treatment regimen may also open chronic totally occluded coronary arteries. The opening of chronic total occlusions (CTOs) is often a difficult problem to address by using percutaneous coronary intervention (PCI), and may also result in complications.

The disclosed treatment regimen is also anticipated to reduce the relapse rate in post-PTCA patients to a level close to 0%. Mortality and recurrent cardiac events after CABG may also be prevented.

The treatment regimen disclosed herein may also be applied to the atheromatous disease of cerebral arteries. Strokes and transient ischemic attacks (TIAs) due to thrombotic episodes may be prevented or their incidence may be reduced. Peripheral vascular disease may also be treated using the disclosed treatment regimen.

The previous description of the disclosed embodiments is provided to enable any person skilled in the art to make or use the invention disclosed herein. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

All references cited herein are expressly incorporated by reference.

What is claimed is:

1. A method of treating coronary artery disease by removing one or more atheromas from one or more coronary arteries of a patient comprising administering a therapeutically effective amount of:
   a. carvedilol;
   b. metformin;
   c. evolocumab; and
   d. one or more statins.

2. The method of claim 1, wherein the one or more statins comprise simvastatin.

3. The method of claim 1, wherein the one or more statins comprise rosuvastatin.

4. A method of treating coronary artery disease by removing one or more atheromas from one or more coronary arteries of a patient comprising administering a therapeutically effective amount of:
   a. carvedilol;
   b. metformin;
   c. evolocumab; and
   d. atorvastatin.

5. The method of claim 1, wherein the one or more statins comprise pravastatin.

* * * * *